United States Patent [19]

Sommerlade

[11] Patent Number: 5,659,067
[45] Date of Patent: Aug. 19, 1997

[54] PREPARATION OF 2,5-BIS(1,1-DIMETHYL-4-HEXYLOXYCARBONYLBUTYL) HYDROQUINONE

[75] Inventor: Reinhard Sommerlade, Freiburg, Germany

[73] Assignee: Ciba-Geigy Corporation, Tarrytown, N.Y.

[21] Appl. No.: 712,720

[22] Filed: Sep. 12, 1996

[30] Foreign Application Priority Data

Sep. 22, 1995 [CH] Switzerland .............. 2679/95

[51] Int. Cl.$^6$ .................................. C07C 69/76
[52] U.S. Cl. ........................................ 560/75
[58] Field of Search ........................... 560/75

[56] References Cited

U.S. PATENT DOCUMENTS 4,484,000 11/1984 Howell ........................ 560/75
4,608,435 8/1986 Howell ........................ 544/87
4,835,323 5/1989 Howell ........................ 568/662

FOREIGN PATENT DOCUMENTS 0069070 2/1986 European Pat. Off. .

*Primary Examiner*—Samuel Barts
*Attorney, Agent, or Firm*—Luther A. R. Hall

[57] ABSTRACT

A description is given of a process for the preparation of 2,5-bis(1,1-dimethyl-4-hexyloxycarbonylbutyl) hydroquinone by reacting 5-methyl-4-hexenoic acid (m)ethyl ester, which is obtainable by reacting 2-hydroxy-2-methyl-3-butene with tri(m)ethyl orthoacetate in the presence of an acid catalyst, with hydroquinone according to Friedel-Crafts, and transesterifying the resulting 2,5-bis(1,1-dimethyl-4-(m)ethoxycarbonylbutyl)-hydroquinone product direct with hexanol in a one-pot process.

10 Claims, No Drawings

PREPARATION OF 2,5-BIS(1,1-DIMETHYL-4-HEXYLOXYCARBONYLBUTYL) HYDROQUINONE

The invention relates to a process for the preparation of 2,5-bis(1,1-dimethyl-4-hexyloxycarbonylbutyl) hydroquinone of the formula VI represented below by alkylation of hydroquinone with the ester of the formula III represented below and subsequent transesterification in a one-pot process.

Hitherto the preparation of the 2,5-bis(5-(m) ethoxycarbonyl-1,1-dimethylbutyl)-hydroquinone intermediate of formula V below started from 5-methyl-5-hexenoic acid methyl ester (EP-A-0069070). Owing to recurring spontaneous polymerisation during the preparation of this starting compound and its purification by distillation, the entire batch must often be discarded and the apparatus be laboriously cleaned. Surprisingly, such problems do not occur when 5-methyl-4-hexenoic acid (m)ethyl ester is used as starting compound. A novel one-pot process has been developed which proceeds via the 5-methyl-4-hexenoic ester of formula III. One-pot alkylation and transesterification achieves a yield advantage of about 15% as against the corresponding two step process. The product is suitable as stabiliser for photosensitive materials (magenta stabiliser for photochemistry, EP-A-0 069 070). At present it is commercially available as Irgaperm ®2140.

According to the invention, the process follows the following formula scheme:

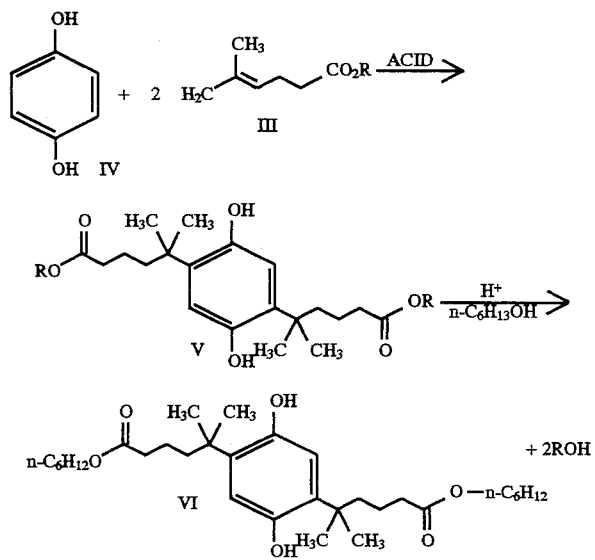

R is $CH_3$ or $C_2H_5$.

Accordingly, the invention relates to a process for the preparation of 2,5-bis(1,1-dimethyl-4-hexyloxycarbonylbutyl)hydroquinone (VI), by reacting
A 5-methyl-4-hexenoic acid (m)ethyl ester (III) with hydroquinone (IV) according to Friedel-Crafts, and
B by transesterifying the resulting 2,5-bis(1,1-dimethyl-4-(m)ethoxycarbonylbutyl)-hydroquinone (V) product direct with hexanol in a one-pot process.

The two steps of the novel process which belong together are the Friedel Crafts alkylation of hydroquinone with compounds of formula III and the subsequent transesterification of the methyl ester or ethyl ester with n-hexanol which is carried out in a one-pot process.

Transesterification is a common method of organic chemistry and is described, inter alia, in Organikum, Berlin 1986; page 388, and in Houben-Weyl, Methoden der organisthen Chemie, Vol.5/1, Stuttgart/NewYork 1985, p. 703 ff.

Suitable catalysts for the transesterification are acids, such as the Brönsted acids cited hereinafter in connection with step A, in particular p-toluenesulfonic acid or sulfuric acid. The transesterification can also be carried out under basic conditions, for example catalysed by alkali metal hydroxides, alkali metal carbonates or alkali metal hydrogen carbonates, metal alcoholates or anion exchangers. Titanium (IV) alkanolates and thallium(I) salts are also suitable. The higher alcohol is conveniently used in excess and the lower alcohol is distilled off. The process is usually carried out at relatively mild temperatures in the range from c. 20° C. to c. 120° C. Suitable solvents are usually the higher alcohols themselves and, in special cases, also solvents which are inert under the reaction conditions, typically chlorinated hydrocarbons and aprotic solvents such as hexamethylphosphoric triamide. As the process of this invention is a one-pot process, the same solvent is expediently use in step A and step B. Alternatively it is also possible to remove the solvent after step A.

The conditions of the Friedel-Crafts alkylation (step A) are described in detail in EP-A-0069068 and EP-A-0106799. Said alkylation is typically carried out in the temperature range from 20° to 170° C., preferably from 100° to 150° C., with catalysis of Brönsted acids, acid earths or Lewis acids.

Suitable Lewis acids are, for example, iron(III) chloride, aluminium chloride, aluminium phenoxide, bortrifluoride or tin(IV) chloride. Suitable Brönsted acids are, in addition to mineral acids such as hydrochloric acid, perchloric acid and sulfuric acid, substituted inorganic acids, typically methane- or ethanesulfonic acids, p-toluenesulfonic acid, organic acids, e.g. dichloroacetic acid, trichloroacetic acid or trifluoroacetic acid, and others more. Acid earths are described in more detail hereinafter. Preferred catalysts for the alkylation described herein are sulfuric acid and p-toluenesulfonic acid.

Conveniently two or more than two moles of ester per mol of hydroquinone are used.

It is possible to work with or without solvent. Common solvents are hydrocarbons, typically benzene, cyclohexane or heptane. Methanol/sulfuric acid mixtures can also be used. In this case the solvent also serves as catalyst. As mentioned above, this one-pot process also entails that the same solvent or solvent mixture is conveniently used in step A and B.

In a preferred embodiment, the starting ester III is prepared by reacting 2-hydroxy-2-methyl-3-butene (I) with tri(m)ethylorthoacetate (II) in the presence of an acid catalyst.

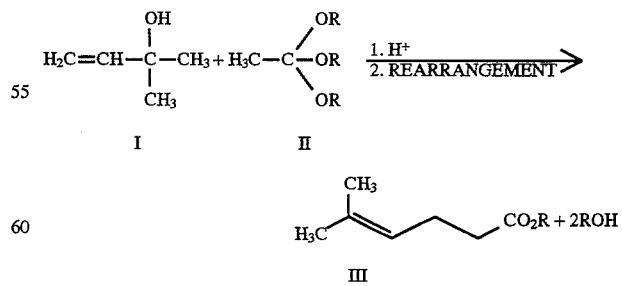

This reaction can be carried out e.g. under the conditions described in JP-A-52-111513.

The reaction temperature is conveniently in the range from 0°–170° C., preferably from 50° to 150° C., most preferably from 100°–120° C. The reaction can be carried out in the presence as well as in the absence of a solvent. The solvents used may be, for example, alkyl aromatics (toluene, xylenes, tetrahydronaphthalene), halogen aromatics or nitroaromatics (chlorobenzene, nitrobenzene), ethers (dioxane, tetrahydrofuran, diethylene glycol dimethyl ether, triethylene glycol dimethyl ether) or chloroalkanes (dichloromethane, chloroform, tetrachloromethane). Orthoester II and allyl alcohol I can be used in a molar ratio of 1:5 to 10:1, preferably of 1:1 to 8:1. The reaction is preferably carried out without any solvent, using excess orthocarbonic acid trialkyl ester. A molar ratio of II:I of 6:1 has been found to be particularly useful, and the excess orthoester which serves as solvent can be recovered by distillation after the reaction is completed and can be used again without any quality problems.

During the reaction the evolving alcohol is expediently distilled off.

Suitable acid catalysts are organic or inorganic acids having a pKa value of about 1.5–5, preferably those having a pKa value of 2.5 to 4.5, more preferably of 4.0 to 4.5, in particular acetic acid, propionic acid and benzoic acid.

Suitable catalysts are usually the following acids:

Organic acids, typically acetic acid, propionic acid, benzoic acid, 2,6-dimethylbenzoic acid, 2,4,6-trimethylbenzoic acid (mesitylene carboxylic acid), ascorbic acid, citric acid, 2,4-dinitrophenol, mineral acids and acid salts such as boric acid, phosphoric acid, potassium dihydrogen phosphate, sodium dihydrogen phosphate, carrier-bound acids (acid ion exchangers, including zeolites), acid earths and naturally occuring or synthetic sheet silicates.

Suitable ion exchange resins are, for example, styrene/divinylbenzene resins which carry sulfonic acid groups, typically Amberlite 200® and Amberlyst®, supplied by Rohm and Haas, or Dowex 50®, supplied by Dow Chemicals; perfluorinated ion exchange resins, typically Nafion H®, supplied by DuPont, or other superacidic ion exchange resins as described in T. Yamaguchi, Applied Catalysis, 61, 1–25 (1990) or M. Hino et al., J. Chem. Soc. Chem. Commun. 1980; 851–852.

Suitable zeolites are, for example, those which are common in petrochemistry as cracking catalysts and which are known as crystalline silicium/aluminium oxides with different crystal structure. Particularly suitable are the faujasites supplied by Union Carbide, e.g. Zeolith X®, Zeolith Y® and ultrastable Zeolith Y®; Zeolith Beta® and Zeolith ZSM-12®, supplied by Mobil Oil Co.; and Zeolith Mordenit®, supplied by Norton.

Suitable naturally occuring sheet silicates are also called acid earths and are, for example, bentonites or montmorillonites which are exploited on a large industrial scale, ground, treated with mineral acids and calcinated. Naturally occuring sheet silicates which are particularly suitable are the Fulcat® types, supplied by Laporte Adsorbents Co., typically Fulcat 22A®, Fulcat 22B®, Fulcat 20® or Fulcat 40®; or the Fulmont® types supplied by Laporte Adsorbents Co., typically Fulmont XMP-3® or Fulmont XMP-4®. A particularly preferred catalyst for the process of this invention is Fulcat 22B®, an acid-activated montmorillonite with 4% of free moisture and an acid titer of 20 mg KOH/g. The other Fulcat® types are likewise to be classified as belonging to this preferred class because there are only minor differences between the individual types such as the number of acid centres.

Modified sheet silicates are also termed "pillared clays" and are derived from the naturally occuring sheet silicates described above, additionally containing between the silicate sheets oxides of, for example, zirconium, iron, zinc, nickel, chromium, cobalt or magnesium, or elements of the rare earths. This type of catalyst is often described in the literature, e.g. by J. Clark et al., J. Chem. Soc. Chem. Commun. 1989, 1353–1354, but is produced only by very few firms. Particularly preferred modified sheet silicates are, for example, Envirocat EPZ-10®, Envirocat EPZG® or Envirocat EPIC®, supplied by Contract Chemicals.

The following Working Example illustrates the invention in more detail:

Example: Preparation of 2,5-bis(1,1-dimethyl-4-hexyloxycarbonylbutyl)-hydroquinone 86.1 g of 2-hydroxy-2-methyl-3-butene are added to 720.9 g of trimethylorthoacetate in a 1500 ml multinecked flask equipped with reflux condenser, stirrer, thermometer and Claisen bridge. After the addition of 4.0 g of benzoic acid as catalyst, the mixture is heated, with stirring, to c. 100° C. and the reflux condenser is thermostated to 65° C.

The reaction mixture is kept at reflux for a total of 8 h and the evolving methanol is continuously distilled off over the Claisen bridge which is thermostated to 65° C. At 2 h intervals, the mixture is cooled for brief periods to 95° C. and a further 2.0 g of catalyst are added each time. Towards the end of the reaction, the temperature rises to c. 112° C. The product is then freed from excess trimethylorthoacetate by vacuum distillation and is purified by fractional distillation. Total amount of the trimethyl orthoacetate recovered by distillation: c. 620 g. Upon completion of the distillation, the residue is cooled to 20°–25° C. and the crude product obtained is purified by fractional distillation, giving c. 125 g of product in the form of a colourless, fruity-smelling liquid, b.p.: 83° C./50 mbar (160° C./1000 mbar); density: 0.917/25° C. Yield: c. 121 g of 5-methyl-4-hexenoic acid methyl ester, corresponding to 84% of theory, based on 2-methyl-3-buten-2-ol.

44 g of hydroquinone, 113.9 g of 5-methyl-4-hexenoic acid methyl ester and 20 g of heptane/methanol 95:5 are placed in a vessel and, with stirring, 7 g of sulfuric acid (98%) are added in a $N_2$ countercurrent at room temperature. The suspension is heated to 90° C. over c. 30 min. The reaction mixture is kept at slight reflux until the onset of crystallisation. Crystallisation begins after c. 20–25 min. After crystallisation, the suspension rapidly becomes viscous. 40 g of heptane/methanol 95:5 are then added dropwise over 10–15 min such that the crystal suspension remains readily stirrable.

The beige viscous suspension is kept for a further 7 h at reflux at 85°–88° C. and then 182 g of 1-hexanol are added dropwise, with stirring, via a dropping funnel.

The reflux condenser is thermostated to 65° C.

The low-viscous readily stirrable suspension is heated to 100°–105° C. and the distillation of methanol is started which is continued at normal pressure up to 105° C. A slight vacuum is then applied and the remainder of the methanol/heptane mixture is distilled off until 105° C./500 mbar is reached.

The distillation receiver is changed and then the pressure is carefully lowered to 100 mbar and kept at 100°–105° C. for a total of 3 h. A further 99 g of 1-hexanol are then added and the mixture is heated to 100°–105° C. and kept at 100°–105° C./100 mbar for 2 h.

Upon completion of the transesterification, excess 1-hexanol is distilled off at a maximum of 105° C./10 mbar (final vacuum). Total amount of distillate: c. 170 g.

The contents of the flask are cooled to 85°–80° C. and 180 g of heptane (isomer mixture) are run in while the temperature is kept at 70° C. 100 ml of deionised water and 10.5 g of sodium hydroxide (30% solution) are run into this solution in succession. The mixture is stirred for 30 min at 70° C. and then stirring is stopped for phase separation and the lower phase is separated off. With stirring, 100 ml of deionised water and 4.4 g of sodium dithionite are run in at 70° C. Stirring is continued for 1 h at 70° C. and then stirring is stopped for phase separation and the lower phase is again separated off.

With stirring, another 100 ml of deionised water are run in and stirring is then continued for a further hour at 70° C. Stirring is then stopped for phase separation and the lower phase is separated off.

Subsequently, the organic product solution is dewatered over a water separator and seeded with some 2,5-bis(1,1-dimethyl-4-hexyloxycarbonylbutyl)hydroquinone crystals at 50° C. and then allowed to cool further until the onset of crystallisation.

The product is isolated via a Büchner funnel and the filter cake is washed with a cold mixture of heptane/methanol and dried in a drying oven at 45° C.

Yield: 171 g of 2,5-bis(1,1-dimethyl-4-hexyloxycarbonylbutyl)hydroquinone, melting point: 159°–161° C.

What is claimed is:

1. A process for the preparation of 2,5-bis(1,1-dimethyl-4-hexyloxycarbonyl-butyl)hydroquinone (VI), which comprises A reacting 5-methyl-4-hexenoic acid (m)ethyl ester(III) with hydroquinone (IV) according to Friedel-Crafts, and B transesterifying the resulting 2,5-bis(1,1-dimethyl-4-(m)ethoxycarbonylbutyl) hydroquinone (V) product direct with hexanol in an one-pot process.

2. A process according to claim 1, wherein the alcohol which evolves as by-product is removed from the reaction mixture by distillation.

3. A process according to claim 1, which comprises carrying out the Friedel-Crafts alkylation A at 80° to 100° C. in the presence of concentrated sulfuric acid as catalyst.

4. A process according to claim 1, wherein the transesterification B is catalysed with sulfonic acid.

5. A process according to claim 1, which comprises preparing the 5-methyl-4-hexenoic acid (m)ethyl ester (III) by reacting 2-hydroxy-2-methyl-3-butene (I) with trimethylorthoacetate or triethylorthoacetate (II) in the presence of an acid catalyst.

6. A process according to claim 5, wherein the reaction is carried out without any additional solvents.

7. A process according to claim 5, wherein the acid catalyst is an acid having a pKa value of 1.5 to 5.

8. A process according to claim 5, wherein the acid catalyst is benzoic acid or propionic acid.

9. A process according to claim 5, wherein the compounds of formulae I and II are used in a molar ratio of 5:1 to 1:10.

10. A process according to claim 5, wherein the reaction temperature is in the range from 100° to 120° C.

* * * * *